United States Patent [19]

Möller et al.

[11] 4,053,621

[45] Oct. 11, 1977

[54] 1-[2-(βNAPHTHYLOXY)ETHYL]-3-METHYL-PYRAZOLONE-(5) AND ANTITHROMBOTIC AND ANTITHROMBOLYTIC COMPOSITIONS AND METHODS UTILIZING THEM

[75] Inventors: Eike Möller, Wuppertal, Germany; Karl Meng, deceased, late of Wuppertal, Germany, by Ilse Heide Frieda Meng, heir; Harald Horstmann, Wuppertal, Germany; Friedel Seuter, Germany; Egbert Wehinger, both of Neviges, Germany

[73] Assignee: Bayer Aktiengesellschaft, Germany

[21] Appl. No.: 582,773

[22] Filed: June 2, 1975

[30] Foreign Application Priority Data

June 6, 1974 Germany .......................... 2427272

[51] Int. Cl.$^2$ ................. A61K 31/295; A61K 31/415; C07D 231/08; C07F 15/02
[52] U.S. Cl. ................. 424/273 P; 424/245; 260/299; 260/310 A; 548/367
[58] Field of Search ............. 260/299, 310 A; 424/273, 245

[56] References Cited

U.S. PATENT DOCUMENTS

| | | | |
|---|---|---|---|
| 2,376,380 | 5/1945 | Porter | 260/305 |
| 2,476,986 | 7/1949 | Martin | 260/310 |
| 2,476,987 | 7/1949 | Martin | 260/310 |
| 2,511,231 | 6/1950 | Weissberger et al. | 95/6 |
| 2,600,788 | 6/1952 | Loria et al. | 95/6 |
| 2,619,419 | 11/1952 | Jennen | 95/6 |
| 2,672,417 | 3/1954 | Jennen | 95/6 |
| 2,681,915 | 7/1954 | Gysin et al. | 260/310 |
| 2,848,446 | 8/1958 | Maderni | 260/147 |
| 3,014,916 | 12/1961 | Wright | 260/310 |
| 3,113,949 | 12/1963 | Bicking | 260/310 |
| 3,147,276 | 9/1964 | Drain et al. | 260/310 A |
| 3,153,654 | 10/1964 | Ficken | 260/310 |
| 3,190,888 | 6/1922 | Wolf et al. | 260/310 |
| 3,558,319 | 1/1971 | Hamaoka et al. | 96/100 |
| 3,563,745 | 2/1971 | Eynde et al. | 96/56.5 |
| 3,615,502 | 10/1971 | Yoshida | 96/56.5 |
| 3,615,506 | 10/1971 | Abbott et al. | 96/56.5 |
| 3,632,818 | 1/1972 | Allais et al. | 260/310 A |
| 3,694,456 | 9/1972 | Noguchi et al. | 260/310 R |
| 3,719,764 | 3/1973 | Girault et al. | 424/273 |
| 3,812,145 | 5/1974 | Sato et al. | 260/310 A |
| 3,823,156 | 7/1974 | Oku et al. | 260/310 A |
| 3,949,083 | 4/1976 | Möller et al. | 424/273 |
| 3,952,008 | 4/1976 | Möller et al. | 260/310 A |
| B 459,408 | 4/1976 | Möller et al. | 424/273 |

FOREIGN PATENT DOCUMENTS

| | | |
|---|---|---|
| 727,091 | 7/1969 | Belgium |
| 2,068,413 | 8/1971 | France |
| 1,003,215 | 8/1957 | Germany |
| 2,230,675 | 1/1974 | Germany |
| 2,230,792 | 1/1974 | Germany |
| 779,703 | 7/1957 | United Kingdom |
| 961,037 | 6/1964 | United Kingdom |
| 599,919 | 3/1948 | United Kingdom |
| 1,190,914 | 5/1970 | United Kingdom |

*Primary Examiner*—Donald G. Daus
*Assistant Examiner*—Diana G. Rivers
*Attorney, Agent, or Firm*—Jacobs & Jacobs

[57] ABSTRACT

1-[2-(β-Naphthyloxy)ethyl]-3-methylpyrazolone-(5) and its salts are useful in the treatment and prophylaxis of thrombotic conditions. The compound is prepared through the reaction of 2-(β-naphthyloxy)ethylhydrazine with either an acetoacetate or an ester of tetrolic acid, or through the condensation of 3-methylpyrazolinone-(5) with a derivative of 2-(β-naphthyloxy)ethane, optionally with subsequent salt formation.

16 Claims, No Drawings

1-[2-(βNAPHTHYLOXY)ETHYL]-3-METHYL-PYRAZOLONE-(5) AND ANTITHROMBOTIC AND ANTITHROMBOLYTIC COMPOSITIONS AND METHODS UTILIZING THEM

DETAILED DESCRIPTION

The present invention pertains to 1-[2-(β-naphthyloxy)ethyl]-3-methylpyrazolone-(5), processes for its preparation, and its use as an antithrombotic agent.

It is known that 3-methylpyrazolones-(5) have antipyretic, analgesic and antiinflammatory activity; see e.g., G. Ehrhardt and H. Ruschig, "Arzneimittel", volume 1, page 148 (1972). However, there is no suggestion that any 3-methylpyrazolone has antithrombotic activity.

The present invention pertains to 1-[2-(β-naphthyloxy)ethyl]-3-methylpyrazolone-(5), which can be represented by formula:

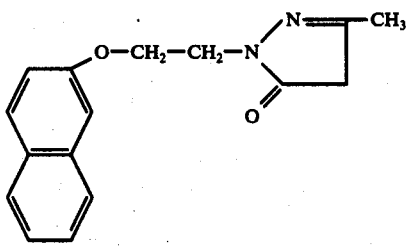

(I)

and to salts thereof. This compound and its salts exhibit powerful antithrombotic properties.

The compound according to the invention can exist in a number of tautomeric forms, or as a mixture of such tautomeric forms, which can be depicted as follows, R¹ denoting the naphthyl-(2)-oxyethyl moiety:

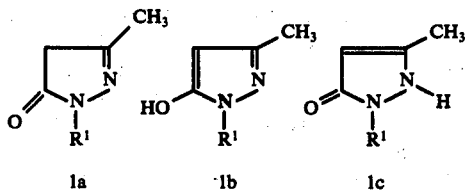

Ia    Ib    Ic

For convenience, throughtout the specification and claims, the above name and formula will be used to represent the compounds of the invention, it being understood that this name and formula include all tautomeric forms of the compounds.

1-[2-(β-Naphthyloxy)ethyl]-3-methylpyrazolone-(5) of the formula (I) is obtained when A. 2-(β-naphthyloxy)ethylhydrazine of the formula:

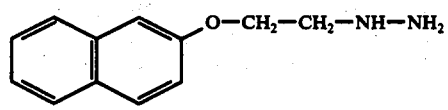

(II)

is reacted with an acetoacetic acid derivative of the formula:

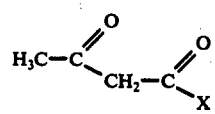

(III)

in which X is alkoxy, aralkoxy, amino or alkylamino, optionally in the presence of inert solvents and a basic or acid catalyst, at temperatures of from 10° to 200° C; when B. 3-methylpyrazolinone-(5) of the formula:

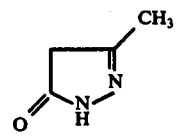

(IV)

is reacted with a 2-(β-naphthyloxy)ethyl derivative of the formula:

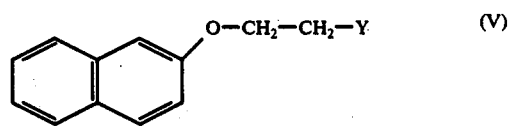

(V)

in which Y is halogeno, or a dialkyloxonium, dialkylsulphonium or trialkylammonium, arylsulphonic acid, alkylsulphonic acid or trifluromethylsulphonic acid radical, optionally in the presence of inert solvents and inorganic or organic bases, at temperatures of from 10° to 200° C, or when C. a tetrolic acid derivative of the formula:

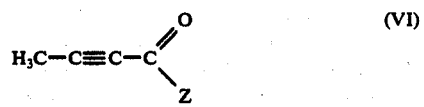

(VI)

in which Z is hydroxyl, alkoxy, aralkoxy, amino or alkylamino, is reacted with 2-(β-naphthyloxy)ethylhydrazine, optionally in the presence of inert solvents and inorganic or organic bases, at a temperature of from 50° to 200° C.

It is surprising that the compounds according to the invention exhibit a powerful antithrombotic action since as noted above pyrazolone-(5) derivatives have not heretofore been regarded as having antithrombotic effects.

Depending on the nature of the starting materials used, the synthesis of the compound according to the invention can be represented by the following illustrative equations:

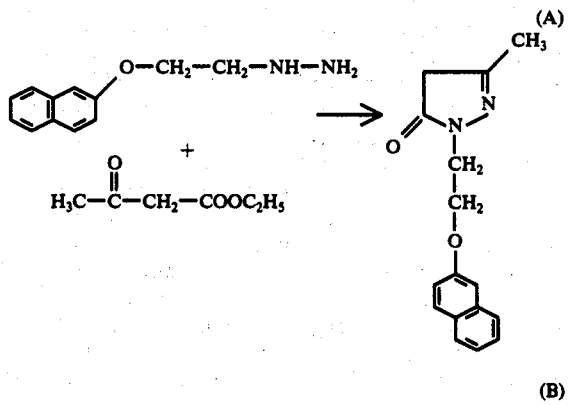

(A)

(B)

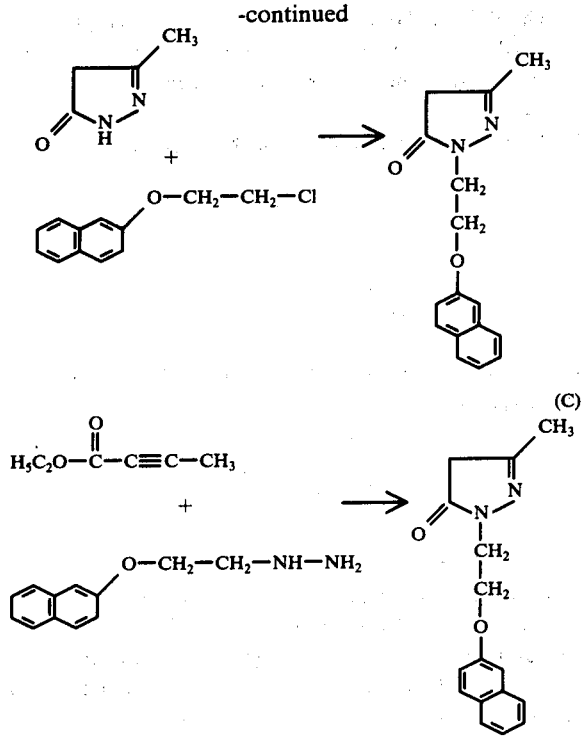

PROCESS VARIANT A

According to process A, the known 2-(β-naphthyloxy)-ethylhydrazine is reacted with an acetoacetic acid derivative of Formula III. In these compounds, X is preferably alkoxy of 1 to 6, especially with 1 to 4, carbon atoms, benzyloxy, amino, alkylamino or dialkylamino, each alkyl group having 1 to 4 carbon atoms. Such acetoacetic acid derivatives are known from the literature or can be prepared according to well known processes; see e.g., D. Borrmann in Houben-Weyl, Methoden der Organischen Chemie, volume VII/4, page 229 et seq. (1968). Typical are the following: acetoacetic acid ethyl ester, acetoacetic acid n-butyl ester, acetoacetic acid propyl ester, acetoacetic acid tert.-butyl ester, acetoacetic acid benzyl ester, acetoacetic acid amide, aceoacetic acid methylamide, acetoacetic acid n-butylamide and acetoacetic acid diethylamide.

Diluents include all inert organic solvents, optionally diluted with water, as for example, hydrocarbons such as benzene, toluene and xylene; halogenohydrocarbons such as methylene chloride, chloroform, carbon tetrachloride and chlorobenzene; alcohols such as methanol, ethanol, propanol, butanol, benzyl alcohol and glycol monomethyl ether; ethers such as tetrahydrofuran, dioxane and glycol dimethyl ether; amides such as dimethylformamide, dimethylacetamide, N-methylpyrrolidone and hexamethylphosphoric acid triamide; sulfoxides such as dimethylsulfoxide, sulfones such as sulfolane and organic bases such such as pyridine, picoline, collidine, lutidine and quinoline.

Basic condensation agents which can be used include inorganic and organic bases, such as alkali metal hydroxides or carbonates such as sodium hydroxide or potassium carbonate, and alcoholates such as sodium or potassium methylate or ethylate. Acid catalysts which can be used are inorganic and organic acids, as for exammple, hydrogen halide acids such as hydrochloric acid or hydrobromic acid, sulphuric acid, and sulphonic acids such as toluenesulphonic acid and trifluoromethylsulphonic acid.

The reaction temperatures can be varied within a wide range and in general, the reaction is carried out at between about 10° and about 200° C, preferably between 20° and 100° C. It is usually carried out under normal pressure but can also be carried out under elevated pressure in closed vessels.

Either the free hydrazine or its acid addition salt can be used as the starting material, and the reaction can also be carried out in the presence of a basic catalyst. The reactants are generally employed in equivalent amounts. After the exothermic initial reaction has ceased, the reaction mixture is preferably stirred, as for example for two to five hours, at elevated temperature and then acidified slightly. The compound thereby obtained can easily be purified by conventional means by recrystallization from a suitable solvent.

PROCESS VARIANT B

According to process B, 3-methylpyrazolinone-(5), which is also known, is reacted with a 2-(β-naphthyloxy)ethyl derivative of Formula V. In these compounds Y is a radical wich is easily removed, such as halogeno, especially chloro or bromo, a dialkyloxonium, dialkylsulphonium or trialkylammonium, an arylsulphonic acid, alkylsulphonic acid or trifluromethylsulphonic acid radical. The alkyl groups mentioned in each case will contain 1 to 4 carbon atoms such as methyl, ethyl, propyl isopropyl, butyl, tert,-butyl or isobutyl, and aryl in particular denotes phenyl, toluyl or naphthyl. These β-naphthyl compounds of Formula V are known or can be prepared according to known processes; see e.g., Kirner et al.; J. Am. Chem. Soc. 51, 3417.

A diluent can be used. These are inert solvents such as hydrocarbons such as benzene, toluene and xylene; alcohols such as methanol, ethanol, propanol, butanol, benzyl alcohol and glycol monomethyl ether; ethers such as tetrahydrofuran, dioxane, and glycol dimethyl ether, amides such as dimethylformamide, dimethylacetamide, N-methylpyrrolidone and hexamethylphosphoric acid triamide; sulfoxides such as dimethylsulfoxide and sulfones such as sulfolane (tetrahydrothiophene-1,1-dioxide).

Bases which can be used include inorganic and organic bases. These preferentially include alkali metal hydroxides and carbonates such as sodium hydroxide, sodium carbonate or potassium hydroxide; alcoholates such as sodium ethylate; and alkali metal hydrides and amides such as sodium hydride or sodium amide.

The reaction temperatures can be varied between about 10° and about 200° C. The reaction is preferably carried out at between 20° and 120° C, usually under normal pressure but can also be carried out under elevated pressure in closed vessels. The reactants are generally present in equimolar amounts.

The compound is readily isolated by distilling off the solvent in vacuo, dissolving the residue in water and slightly acidifying the aqueous mixture. It can be purified by recrystallization.

PROCESS VARIANT C

According to process C, the known 2-(β-naphthyloxy)-ethylhydrazine of Formula II is reacted with a tetrolic acid derivative of Formula VI. In these compounds Z is preferably hydroxyl of 1 to 6, especially with 1 to 2, carbon atoms, benzyloxy, amino, alkylamino or dialkylamino, each with 1 to 4 carbon atoms per alkyl group. These groups may be optionally substituted. The tetrolic acid derivatives of Formula VI are known or can be prepared according to methods known from the literature; see, e.g., Beilsteins "Handbuch der Organischen Chemie" 2, 480 (1920); ibid. 2, III 1,447 et seq. (1961). Typical of these are tetrolic acid methyl ester, tetrolic acid ethyl ester, tetrolic acid n-butyl ester, tetrolic acid isopropyl ester, tetrolic acid tert.-butyl ester, tetrolic acid benzyl ester, tetrolic acid amide, tetrolic acid methylamide, tetrolic acid n-butylamide, tetrolic acid dimethylamide and tetrolic acid diethylamide.

Diluents which can be used include all inert organic solvents optionally diluted with water, recited above.

Inorganic and organic bases can be used are the basic condensation agents described above.

The reaction temperatures can be varied within a wide range and, in general, the reaction is carried out at temperatures from about 50° and about 200° C, preferably between 70° and 150° C. It too is usually carried out under normal pressure but can also be conducted under elevated pressure in closed vessels. The reactants are employed in equimolar amounts. The compound according to the invention, obtained in a crystalline form after evaporation of the diluent, can be readily purified by recrystallization.

The invention also relates to the use in human and veterinary medicine of the compounds of the invention in combatting thrombembolic conditions.

The compounds of the present invention are administered parenterally or orally in any of the usual pharmaceutical forms. These include solid and liquid oral unit dosage forms such as tablets, capsules, powders, suspensions, solutions, syrups and the like, including sustained release preparations, and fluid injectable forms such as sterile solutions and suspensions. The term unit dosage form as used in this specification and the claims refer to physically discrete units to be administered in single or multiple dosage to animals, each unit containing a predetermined quantity of active material in association with the required diluent, carrier or vehicle. The quantity of active material is that calculated to produce the desired therapeutic effect upon administration of one or more of such units.

Powders are prepared by comminuting the compound to a suitable fine size and mixing with a similarly comminuted diluent pharmaceutical carrier such as an edible carbohydrate material as for example, starch. Sweetening, flavoring, preservative, dispersing and coloring agents can also be present.

Capsules are made by preparing a powder mixture as described above and filling formed gelatin sheaths. A lubricant such as talc, magnesium stearate and calcium stearate can be added to the powder mixture as an adjuvant before the filling operation; a glidant such as colloidal silica may be added to improve flow properties; a disintegrating or solubilizing agent may be added to improve the availability of the medicament when the capsule is ingested.

Tablets are made by preparing a powder mixture, granulating or slugging, adding a lubricant and disintegrant and pressing into tablets. A powder mixture is prepared by mixing the compound, suitably comminuted, with a diluent or base such as starch, sucrose, kaolin, dicalcium phosphate and the like. The powder mixture can be granulated by wetting with a binder such as syrup, starch paste, acacia mucilage or solutions of cellulosic or polymeric materials and forcing through a screen. As an alternative to granulating, the powder mixture can be run through the tablet machine and the resulting imperfectly formed slugs broken into granules. The granules can be lubricated to prevent sticking to the tablet forming dies by means of the addition of stearic acid, a stearate salt, talc or mineral oil. The lubricated mixture is then compressed into tablets. The medicaments can also be combined with free flowing inert carriers and compressed into tablets directly without going through the granulating or slugging steps. A protective coating consisting of a sealing coat of shellac, a coating of sugar or polymeric material and a polish coating of wax can be provided. Dyestuffs can be added to these coatings to distinguish different unit dosages.

Oral fluids such as syrups and elixirs can be prepared in unit dosage form so that a given quantity, e.g., a teaspoonful, contains a predetermined amount of the compound. Syrups can be prepared by dissolving the compound in a suitably flavored aqueous sucrose solution while elixirs are prepared through the use of a non-toxic alcoholic vehicle. Suspensions can be formulated by dispersing the compound in a non-toxic vehicle in which it is insoluble.

Fluid unit dosage forms for parenteral administration can be prepared by suspending or dissolving a measured amount of the compound in a non-toxic liquid vehicle suitable for injection such as an aqueous or oleaginous medium and sterilizing the suspension or solution. Alternatively a measured amount of the compound is placed in a vial and the vial and its contents are sterilized and sealed. An accompanying vial or vehicle can be provided for mixing prior to administration.

In the case of parenteral use, it is particularly advantageous to combine compounds according to the invention in a suitable solvent with an equimolar amount of a nontoxic inorganic or organic base. Sodium hydroxide solution, potasssium hydroxide solution, ethanolomine, diethanolamine, triethanolamine, amino-tris-hydroxymethyl-methane, glucosamine and N-methylglucosamine may be meantioned as examples.

Such salts, namely the nontoxic alkali metal, alkaline earth, aluminum, iron and organic base (amine) salts can also be of increased importance for oral use of the compounds according to the invention, in that they accelerate or delay the resorption, as desired. In addition to the salts already mentioned, there may be named as examples the magnesium, calcium, aluminum and iron salts.

In general it has proved advantageous, in the case of parenteral administration, to administer amounts of about 0.01 to 50 mg/kg of body weight, preferably about 0.1 to 10 mg/kg of body weight, per day, in order to achieve effective results, while in the case or oral administration the dosage is about 0.1 to 500 mg/kg of body weight, preferably 0.5 to 100 mg/kg of body weight, per day.

It can at times be necessary to deviate from these dosages and in particular to do so in accordance with the body weight of the test animal, the nature of the method of administration, the species of animal and its individual response, the type of formulation and the interval at which it is administered. Thus it may suffice in some cases to use less than the above-mentioned minimum amount while in others the upper limit mentioned must be exceeded. Where large amounts are administered, these can be divided into several individual administrations over the course of the day.

The examples which follow are typical formulation procedure:

a. 500 g of 1-[2-(β-naphthyloxy)ethyl]-3-methylpyrazolone-(5) are comminuted to a powder, mixed with 300 g of lactose and 200 g of potato starch, moistened with an aqueous gelatin solution and then granulated by passing through a sieve. After drying, 60 g of talc and 5 g of sodium laurylsuphate are added and the mixture is pressed to form 10,000 tablets, each containing 50 mg of active compound.

b. 50 g of the sodium salt of 1-[2-(β-naphthyloxy)ethyl]-3-methylpyrazolone-(5) are dissolved in 1,000 ml of propylene glycol and the solution is made up to 2,000 ml with water. This solution is introduced, inder aceptic conditions, into sterile ampoules of 5 ml capacity each, each ampoule containing 50 mg of active compound.

The antithrombotic action of the compound according to the invention can be conveniently observed in laboratory models, of which the following is typical.

The left jugular veins of rats weighing 170-180 g were exposed under ether narcosis and supercooled to −12° C for 2 minutes to stimulate thrombus formation. Four hours later, the thrombus was isolated from the vein and weighed. The test animals were given the test preparation in tragacanth mucilage immediately before supercooling the wall of the vein. The protective antithrombotic activity was tested within the first 4 hours after stimulating thrombus formation.

thrombolytic effects were only achievable by repeated intravenous administration of toxic fibrinolytics such as streptokinase and urokinase, while the compound according to the invention is adminstered orally and only once per day.

To demonstrate the thrombolytic effect, narcotized male rats are used. The left jugular vein is exposed and briefly cooled to -12° C. This damages the wall of the vein so that a thrombus is produced, which grows to its maximum size over the course of 4 hours. The compound according to the invention is administered orally 24 hours and 26 hours after producing the thrombosis. In contrast, streptokinase (used for comparison) can only be administered intravenously since it is completely inactive after oral administration. Four hours after the first administration, the thrombi are removed from the vein and weighed. The thrombolytic effect is detected by comparison with a control group to which the solvents, without active compounds, were administered in the same way. The results are shown in Table 2.

After two intravenous injections of 10,000 U/kg, streptokinase, which is fibrinolytically active, reduces the thrombus weight over the course of 4 hours from 351 ± 53 to 194 ± 64 μg; i.e., 45%. The compound according to the invention has the same effect after two oral administrations of 10 mg/kg. The thrombus weight is reduced from 288 ± 26 to 147 ± 16 μg; i.e., 49%.

Table 2:

| | Thrombolytic effect/rats | | Difference and significance, relative to control |
|---|---|---|---|
| | Number of animals | Thrombus weight, μg | |
| Control, administered orally | 93 | 288 ± 26 | — |
| Compound according to the invention 2 × 10 mg/kg, administered orally | 84 | 147 ± 16 | −49% |
| Control, administered intravenously | 23 | 351 ± 53 | — |
| Streptokinase, administered intravenously 2 × 10,000 U/kg i.v. | 21 | 194 ± 64 | −45% |
| Streptokinase, administered orally | | | no effect |

The results of the investigations with the compound according to the invention are shown in the table which follows:

Table 1

| | Control on animals without active compound | Animals treated with the compound according to the invention (100 mg/kg administered orally) |
|---|---|---|
| Size of thrombus in μg Average value | 115 ± 12 | 53 ± 10 |
| Number of experiments | 18 | 16 |

The experiments show that the compound according to the invention significantly inhibits the formation of venous thrombi. After a treatment period of 4 hours, the size of the thrombi is reduced by 54%.

The product of the process can therefore be used for the prophylaxis of thrombembolic diseases. In addition to the inhibiting effect on the formation of thrombi, the compound according to the invention is also distinguished by a very powerful thrombolytic effect since depositions already formed are redissolved under the influence of the compound. Hitherto corresponding

EXAMPLE 1

13 g. (0.1 mol) of ethyl acetoacetate in 20 ml of absolute ethanol were added to 20.2 g (0.1 mol) of 2-(β-naphthyloxy)-ethylhydrazine in a little absolute ethanol. After the exothermic initial reaction had ceased, the reaction mixture was heated for 2 hours under reflux.

On cooling the crude product crystallized out. It was purified by recrystallization from an ethanol/dimethylformamide mixture (10:1). Yield: 82% of theory. Melting point: 162°-164° C.

EXAMPLE 2

Analogously to Example 1, tert.-butyl acetoacetate and b 2-(β-naphthyloxy)-ethylhydrazine gave 1-(β-naphthyloxy)-ethyl)-3-methylpyrazolone-(5) according to the invention.

EXAMPLE 3

The compound according to the invention was obtained in approx. 75% yield from benzyl acetoacetate and 2-(β-naphthyloxy)-ethylhydrazine under the reaction conditions of Example 1.

EXAMPLE 4

19.6 g of 3-methyl-pyrazolone-(5) were added in portions to a suspension of 10.0 g of sodium hydride in 200 ml of absolute dimethylformamide.

After the evolution of hydrogen has ceased, 41.2 g of b 2-(β-naphthyloxy)ethyl chloride were added dropwise to the reaction solution. The mixture was then stirred for 2 hours at 60° C, the solvent was distilled off in vacuo, the residue was taken up in water and the solution was acidified with dilute acetic acid.

The crude product thereby obtained was recrystallized from an ethanol/dimethylformamide mixture. Yield: 28% of theory. Melting point: 162°–164° C.

EXAMPLE 5

9.8 g of 3-methylpyrazolone-(5) and 25.1 g of 2-(naphthyloxy)-ethyl bromide were thoroughly triturated and slowly heated to 110° C in a reaction vessel. The melt thereby produced was heated for a further 4 hours at approx. 110° C. The crystal paste obtained after cooling was dissolved in a hot mixture of dimethylformamide and ethanol. The crystals obtained after the solution has crystallized out were purified by a further recrystallization. Yield: 38% Melting point: 162°–164° C.

EXAMPLE 6

8.3 g (0.074 mol) of tetrolic acid ethyl ester and 14.8 g of 2-(β-naphthyloxy)-ethylhydrazine in 70 ml of n-butanol were heated for 8 hours under reflux.

The reaction solution was then concentrated and the solid residue was twice recrystallized from an ethanol/dimethylformamide mixture (10:1). Yield: 45% of theory. Melting point: 162°–164° C.

EXAMPLE 7

The compound according to the invention was obtained analogously to Example 4 from tetrolic acid methyl ester and 2-(β-naphthyloxy)-ethylhydrazine.

EXAMPLE 8

On reacting tetrolic acid benzyl ester and 2-(β-naphthyloxy)-ethylhydrazine, the compound according to the invention was obtained in approx. 40% yield if the reaction was carried out in accordance with the conditions of Example 4.

What is claimed is:

1. 1-[2-(β-naphthyloxy)ethyl]-3-methylpyrazolone-(5) or a pharmaceutically acceptable nontoxic salt thereof.

2. The compound according to claim 1 which is 1-[2-(β-naphthyloxy)ethyl]-3-methylpyrazolone-(5).

3. A method of inhibiting thrombus formation and of reducing or redissolving a thrombus in humans and animals which comprises administering to a human or animal in need thereof an antithrombotically effective amount or an antithrombolytically effective amount of a compound according to claim 1.

4. A pharmaceutical composition useful for inhibiting thrombus formation and for reducing or redissolving a thrombus in humans and animals which comprises an antithrombotically effective amount or an antithrombolytically effective amount of a compound according to claim 1 in combination with a pharmaceutically acceptable carrier or diluent.

5. An alkali metal, alkaline earth metal, aluminum, iron or organic base salt of 1-[2-(β-naphthyloxy)ethyl]-3-methylpyrazolone-(5) according to claim 1.

6. The magnesium, calcium, aluminum, iron or sodium salt of 1-[2-(β-naphthyloxy)ethyl]-3-methylpyrazolone-(5) according to claim 1.

7. The method according to claim 3 wherein the compound is an alkali metal, alkaline earth metal, aluminum iron or organic base salt of 1-[2-(β-naphthyloxy)ethyl]-3-methylpyrazolone-(5).

8. A method according to claim 3 wherein the compound is 1-[2-(β-naphthyloxy)ethyl]-3-methylpyrazolone-(5).

9. A method according to claim 3 wherein the compound is the magnesium, calcium, aluminum, iron or sodium salt of 1-[2-(β-naphthyloxy)ethyl]-3-methylpyrazolone-(5).

10. A method according to claim 3 wherein the administration is oral.

11. A method according to claim 3 wherein the administration is parenteral.

12. A pharmaceutical composition according to claim 4, wherein the compound is an alkali metal, alkaline earth metal, aluminum, iron or organic base salt of 1-[2-(β-naphthyloxy)ethyl]-3-methylpyrazolone-(5).

13. A pharmaceutical composition according to claim 4 wherein the compound is 1-[2-(β-naphthyloxy)ethyl]-3-methylpyrazolone-(5).

14. A pharmaceutical composition according to claim 4 wherein the compound is the magnesium calcium, aluminum, iron or sodium salt of 1-[2-(β-naphthyloxy)ethyl]-3-methylpyrazolene-(5).

15. A pharmaceutical composition according to claim 4 in oral administration form.

16. A pharmaceutical composition according to claim 4 in parental administration form.

* * * * *